(12) United States Patent
Qu et al.

(10) Patent No.: US 11,883,178 B2
(45) Date of Patent: Jan. 30, 2024

(54) METHOD AND SYSTEM TO DETECT P-WAVES IN CARDIAC ARRHYTHMIC PATTERNS

(71) Applicant: Pacesetter, Inc., Sylmar, CA (US)

(72) Inventors: Fujian Qu, San Jose, CA (US); Nima Badie, Berkeley, CA (US); Jong Gill, Valencia, CA (US)

(73) Assignee: Pacesetter, Inc., Sylmar (CA)

(*) Notice: Subject to any disclaimer, the term of this patent is extended or adjusted under 35 U.S.C. 154(b) by 157 days.

(21) Appl. No.: 17/675,345

(22) Filed: Feb. 18, 2022

(65) Prior Publication Data

US 2022/0167906 A1    Jun. 2, 2022

Related U.S. Application Data

(63) Continuation of application No. 16/991,421, filed on Aug. 12, 2020, now Pat. No. 11,284,828.

(51) Int. Cl.
| | |
|---|---|
| *A61B 5/361* | (2021.01) |
| *A61B 5/35* | (2021.01) |
| *A61B 5/316* | (2021.01) |
| *A61B 5/00* | (2006.01) |
| A61B 5/363 | (2021.01) |

(52) U.S. Cl.
CPC .............. *A61B 5/361* (2021.01); *A61B 5/316* (2021.01); *A61B 5/35* (2021.01); *A61B 5/7264* (2013.01); *A61B 5/363* (2021.01); *A61B 5/686* (2013.01)

(58) Field of Classification Search
None
See application file for complete search history.

(56) References Cited

U.S. PATENT DOCUMENTS

| | | |
|---|---|---|
| 8,135,456 B2 | 3/2012 | Haluska |
| 8,594,775 B2 | 11/2013 | Ghosh et al. |
| 2006/0129196 A1 | 6/2006 | Dong et al. |

(Continued)

FOREIGN PATENT DOCUMENTS

| | | |
|---|---|---|
| AP | 3566744 A1 | 11/2019 |
| EP | 3566746 A1 | 11/2019 |

OTHER PUBLICATIONS

Extended European Search Report for EP Application No. 19172677.7-1124 dated Sep. 26, 2019 (7 pages).

(Continued)

*Primary Examiner* — Kennedy Schaetzle
(74) *Attorney, Agent, or Firm* — Dean D. Small; The Small Patent Law Group, LLC

(57) ABSTRACT

A computer implemented method for detecting arrhythmias in cardiac activity including obtaining far field cardiac activity (CA) signals for a series of beats. For at least a portion of the beats, the one or more processors perform, on a beat by beat basis: a) identifying first and second feature of interests (FOI) from a segment of the CA signal that corresponds to a current beat; and b) classifying the current beat into one of first and second groups. The method also includes designating one of the first and second groups to be a primary group based on a relation between the first and second groups, and for the beats in the primary group, selecting one of the first and second FOIs as the R-wave FOI. The method also includes rejecting an arrhythmia detection based on the P-waves detected.

20 Claims, 12 Drawing Sheets

(56) References Cited

U.S. PATENT DOCUMENTS

| | | |
|---|---|---|
| 2006/0217621 A1 | 9/2006 | Kim et al. |
| 2009/0281587 A1 | 11/2009 | Pei |
| 2010/0106209 A1 | 4/2010 | Gunderson et al. |
| 2011/0125206 A1 | 5/2011 | Bornzin et al. |
| 2014/0128758 A1 | 5/2014 | Galloway et al. |
| 2016/0213270 A1 | 7/2016 | Cao et al. |
| 2016/0235317 A1 | 8/2016 | Sarkar et al. |
| 2017/0251940 A1 | 9/2017 | Perschbacher et al. |
| 2019/0336031 A1* | 11/2019 | Malhotra ............... A61B 5/361 |
| 2019/0336083 A1 | 11/2019 | Gill et al. |
| 2020/0237314 A1 | 7/2020 | Qu et al. |

OTHER PUBLICATIONS

Firoozabadi "P-wave Analysis in Atrial Fibrillation Detection Using a Neural Network Clustering Algorithm" Computing in Cardiology, 2018 (4 pages).

Extended European Search Report for corresponding EP Application No. 21185150.6-1122 dated Jan. 18, 2022.

* cited by examiner

METHOD AND SYSTEM TO DETECT P-WAVES IN CARDIAC ARRHYTHMIC PATTERNS

REFERENCE TO RELATED APPLICATIONS

The present application is a continuation application of, and claims priority to, U.S. application Ser. No. 16/991,421, Titled "METHOD AND SYSTEM TO DETECT P-WAVES IN CARDIAC ARRHYTHMIC PATTERNS" which was filed on 12 Aug. 2020, the complete subject matter of which is expressly incorporated herein by reference in its entirety.

FIELD OF THE INVENTION

Embodiments herein relate generally to implantable medical devices, and more particularly to detection and discrimination of an underlying arrhythmic events based on P-waves.

RELATED APPLICATIONS

The following applications relate to and are filed concurrently on the same day as the present application, and are expressly incorporated herein by reference in their entireties (hereafter referred to as "Co-Pending Related Applications"):

U.S. patent application Ser. No. 15/973,126, titled "METHOD AND SYSTEM FOR SECOND PASS CONFIRMATION OF DETECTED CARDIAC ARRHYTHMIC PATTERNS", U.S. patent application Ser. No. 15/973,351, titled "METHOD AND SYSTEM TO DETECT R-WAVES IN CARDIAC ARRHYTHMIC PATTERNS", U.S. patent application Ser. No. 15/973,307, titled "METHOD AND SYSTEM TO DETECT POST VENTRICULAR CONTRACTIONS IN CARDIAC ARRHYTHMIC PATTERNS", and U.S. patent application Ser. No. 15/973,384, titled "METHOD AND SYSTEM TO DETECT NOISE IN CARDIAC ARRHYTHMIC PATTERNS".

BACKGROUND OF THE INVENTION

Today, numerous atrial fibrillation (AF) detection processes are implemented within implantable cardiac monitors (ICMs) that detect atrial fibrillation based on irregularities and variation patterns in RR intervals. In some embodiments, the AF detection process steps beat by beat through cardiac activity (CA) signals and analyzes the RR intervals over a period of time. An AF detection is declared when the RR interval pattern for the suspect beat segments is sufficiently dissimilar from RR interval patterns for sinus beat segments.

However, AF detection processes may exhibit false AF detection where the ICM provides a device documented AF episode, even though a patient is not experiencing AF. False AF detection may arise due to various conditions and behavior of the heart, such as when a patient experiences sick sinus syndrome with irregular RR intervals, frequent premature atrial/ventricular contractions (PACs/PVCs) and/or inappropriate R-wave sensing. To an extent, false AF detection is due, in part, to dependence of the AF detection process upon identification of R-wave features, with little or no input concerning other features of a cardiac event.

Algorithms have been developed for ICMs for AF detection that include mechanisms for detecting R-R interval irregularities, and rejecting false detections due to bigeminy/trigeminy or lack of sudden onset. Software has also been developed in which a P wave detection discriminator was introduced to further reduce false positive detections due to irregular sinus rhythm. While these additional algorithms effectively reduce the number of false AF episodes, false detections remain to be significant in some devices.

In particular, several scenarios still exist where false AF episode may be detected. First, even when R wave sensing is appropriate, device sensed markers are not consistently placed on the same features of the R wave. The shift of R wave markers can be substantial for certain types of QRS morphologies (e.g. BBB shown in FIG. 3A and biphasic waveforms in FIG. 3B). As a result, the P-wave segments are misaligned. As shown in FIG. 3C, the ensemble average (thick green trace) is a blend of two alignment groups, and thus unlikely to match with any individual P-wave.

Second, P-waves are not aligned in patients with a large degree of P-R interval variation. FIG. 3D shows an example of the ensemble average template vs individual P-waves under varying P-R intervals.

Third, a few outliers due to baseline drift or motion artifact in the EGM signal can distort the ensemble average template morphology from real P waves. FIG. 3E shows an example of the ensemble average template vs individual P waves with and without the outliers.

SUMMARY

In accordance with embodiments herein, a computer implemented method for detecting arrhythmias in cardiac activity is provided that includes, under control of one or more processors configured with specific executable instructions, obtaining far field cardiac activity (CA) signals for a series of beats. For at least a portion of the beats in the CA signal, the one or more processors perform the following on a beat by beat basis: a) identifying first and second feature of interests (FOI) from a segment of the CA signal that corresponds to a current beat; and b) classifying the current beat into one of first and second groups based on a relation between the first and second FOIs for the current beat. The one or more processors also designate one of the first and second groups to be a primary group based on a relation between the first and second groups, and for the beats in the primary group, select one of the first and second FOIs as the R-wave FOI. The one or more processors also position a P-wave detection window over the CA signal in connection with at least a portion of the beats based on the R-wave FOI for the corresponding beat, detect P-waves in the P-wave detection window over the CA signals, and reject an arrhythmia detection based on the P-waves detected.

Optionally, the one or more processors align the R-wave FOIs and the corresponding segments of the CA signals within one another for at least a portion of the series of beats based on the R-wave FOIs. In one aspect, the first and second FOI corresponds to positive and negative peak values of the corresponding beat, the classifying further comprising classifying beats into the first group for which the positive peak value is greater than the negative peak value and classifying beats into the second group, for which the negative peak value is greater than the positive peak value. In another aspect, the R-wave FOI corresponds to the R-wave peak, the marking including marking peak values of the beats in the primary group as the R-wave peak. In one example, the relation represents a popularity relation, the designating further comprises designating, as the primary group, the one of the first and second groups that includes more beats.

Optionally, the first group represents the primary group and the second group represents a secondary group, and the method also includes for at least a portion of the beats in the secondary group, performing the following on a beat by beat basis g1) comparing the first and second FOIs and based thereon, labeling one of the first and second FOIs to represent a minor FOI for the corresponding beat; and g2) when the first and second FOI are within a tolerance range of one another, marking the minor FOI as the R-wave FOI for the corresponding beat in the secondary group. In another aspect, the method includes calculating a moving combination for the CA signals to form a composite CA signal, the moving combination configured to at least partially remove non-noise artifact displacement (NAD) due to a physiologic condition, the identifying, classifying, designating and marking based on the composite CA signals. Alternatively, the moving combination is configured to at least partially remove a notch in the CA signals, representing the NAD.

Optionally, the method also includes identifying the beats that have outlier P-waves, the outlier P-waves having peak to peak amplitudes that are not within a pattern of a distribution of P-wave peak to peak amplitudes for at least a portion of the beats. In another aspect the method also includes determining a median peak time for the P-waves detected; and determining a peak displacement between a peak time of each of the P-waves detected and the determined median peak time. Alternatively, determining if the peak displacement between the peak time of each of the P-waves detected exceeds a threshold displacement. In one aspect, the method includes shifting a peak of a P-wave of the P-waves detected to align with a median peak of the P-waves detected. In another aspect the method includes forming a P-wave segment ensemble template based on the P-waves detected; comparing a P-wave segment to the P-wave segment ensemble template to determine a signal to noise ratio of the P-wave segment; and rejecting the P-wave segment when the signal to noise ratio is above a threshold value.

In one or more embodiments, a system for detecting arrhythmias in cardiac activity, includes a memory to store specific executable instructions, and one or more processors configured to execute the specific executable instructions. The one or more processors obtain far field cardiac activity (CA) signals for a series of beats. For at least a portion of the beats in the CA signal, the one or more processors perform the following on a beat by beat basis: a) identifying first and second feature of interests (FOI) from a segment of the CA signal that corresponds to a current beat; and b) classifying the current beat into one of first and second groups based on a relation between the first and second FOIs for the current beat. The one or more processors also designate one of the first and second groups to be a primary group based on a relation between the first and second groups, and for the beats in the primary group, mark a select one of the first and second FOIs as the R-wave FOI. The one or more processors also position a P-wave detection window over the CA signal in connection with at least a portion of the beats based on the R-wave FOI for the corresponding beat, detect P-waves in the P-wave detection window over the CA signals, and reject arrhythmia detections based on the P-waves detected.

Optionally, the one or more processors are further configured to execute the specific executable instructions for: aligning the R-wave FOIs and the corresponding segments of the CA signals within one another for at least a portion of the series of beats based on the R-wave FOIs. In one aspect, the first and second FOI corresponds to positive and negative peak values of the corresponding beat, the classifying further comprising classifying beats into the first group for which the positive peak value is greater than the negative peak value and classifying beats into the second group, for which the negative peak value is greater than the positive peak value. In another aspect, the R-wave FOI corresponds to the R-wave peak, the marking including marking peak values of the beats in the primary group as the R-wave peak. In one example, the relation represents a popularity relation, the designating further comprises designating, as the primary group, the one of the first and second groups that includes more beats.

Optionally, the one or more processors are further configured to execute the specific executable instructions for: identifying the beats that have outlier P-waves, the outlier P-waves having peak to peak amplitudes that are not within a pattern of a distribution of P-wave peak to peak amplitudes for at least a portion of the beats. In one aspect, the one or more processors are further configured to execute the specific executable instructions for: determining a median peak time for the P-waves detected; and determining a peak displacement between a peak time of each of the P-waves detected and the determined median peak time. In another aspect, the one or more processors are further configured to execute the specific executable instructions for: determining if the peak displacement between the peak time of each of the P-waves detected exceeds a threshold displacement.

DETAILED DESCRIPTION

Figure 1:
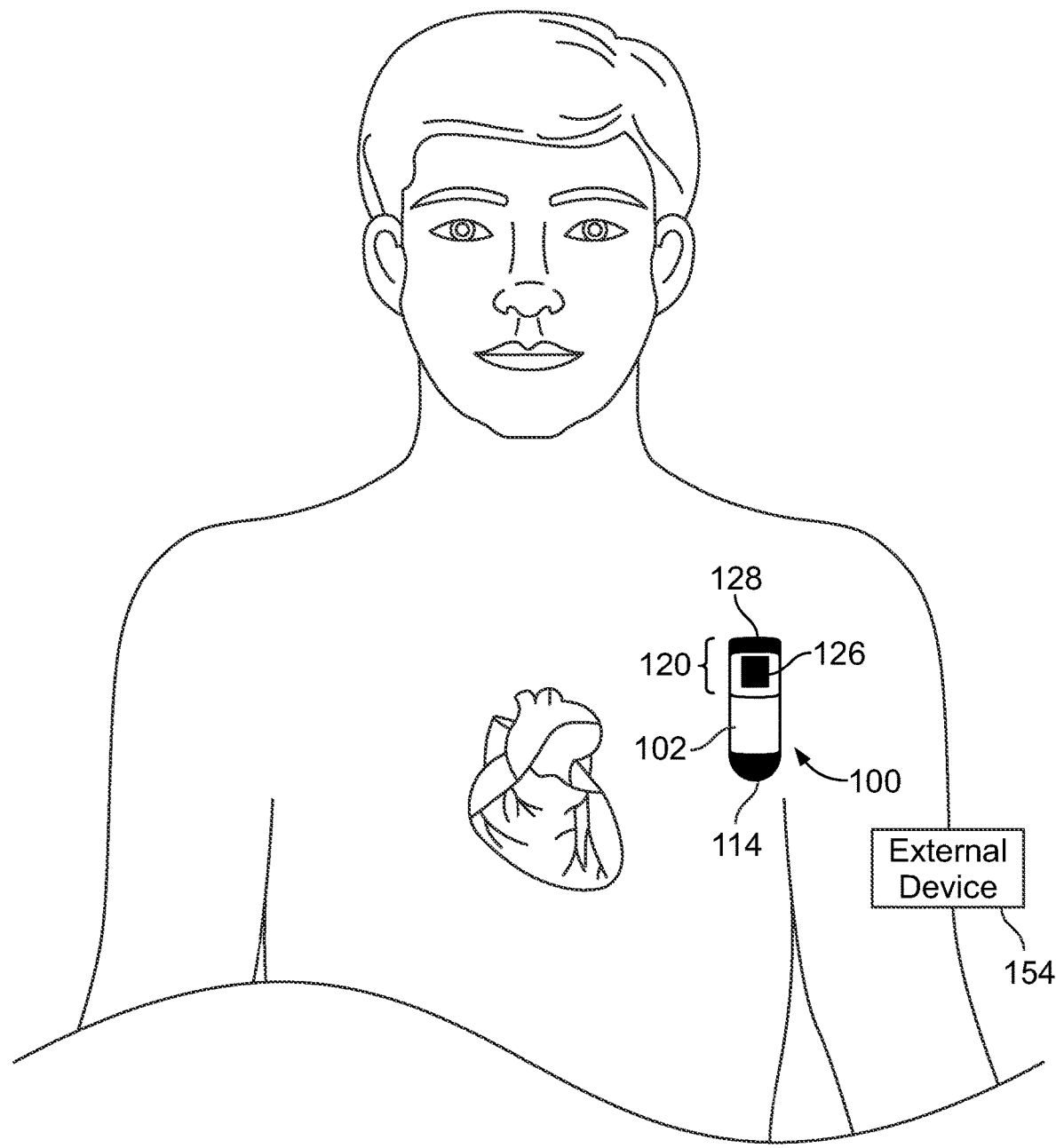
FIG. 1 illustrates an implantable cardiac monitoring device (ICM) intended for subcutaneous implantation at a site near the heart in accordance with embodiments herein.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further non-limiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "FOI" refers to a feature of interest within CA signals. Non-limiting examples of features of interest include an R-wave, P-wave, T-wave, and isoelectric segments. A feature of interest may correspond to a peak of an individual R-wave, an average or median P, R or T-wave peak and the like.

The terms "beat" and "cardiac event" are used interchangeably and refer to both normal or abnormal events.

The term "real-time" refers to a time frame contemporaneous with a normal or abnormal episode occurrence. For example, a real-time process or operation would occur during or immediately after (e.g., within minutes or seconds after) a cardiac event, a series of cardiac events, an arrhythmia episode, and the like.

The term "sensitivity level", as used herein, refers to a threshold that an input CA signal must exceed for an implantable device to identify a QRS complex feature of interest (e.g., an R-wave). As one non-limiting example, software may be implemented using a programmed sensitivity level to declare an R-wave to be detected when the input CA signal exceeds the current programmed sensitivity level. In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with an amplitude of 0.14 mV will not be detected as an R-wave.

The term "detection window", as used herein, refers to a period of time during which a cardiac event is detected or analyzed. In examples, the cardiac event may be the formation of a P-wave, where the detection window of the P-wave, or P-wave detection window, represents the period of time during which the P-wave is determined to be formed. In this manner, the detection window may be measured in milliseconds.

Provided are methods and systems for analyzing CA signals in a manner to reduce false AF detections and increase overall accuracy of AF determinations for devices that monitor the heart, including ICMs, subcutaneous ICDs, or the like. To reduce false detections, R-wave alignment is provided such that instead of using the device-sensed R-wave markers as a reference point, R-waves are aligned in the P-wave analysis window by their peaks. After the alignment, the P-wave segment boundaries are adjusted either to the left or right relative to the R-wave peak. In addition, after extracting a P-wave segment from qualified beats and signal detrending, outlier P-wave segments are identified and excluded from the systems and method. The methods and systems also provide for P-wave alignment before calculating an ensemble-average P-wave template signal. This step is added to address the P-R interval variation. Finally, to check morphology consistency of a P-wave segment, a fixed threshold is utilized to determine if the individual P-wave segment has the same morphology and amplitude as a P-wave segment ensemble template. In this manner, existing values that form the P-wave segment ensemble template are utilized to calculate the signal-to-noise ratio and confirm P-wave detection if the signal-to-noise ratio exceeds a threshold.

FIG. 1 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. In one example, far field CA signals for a series of beats are obtained. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 114 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a processor for identifying FOIs from a CA signal that corresponds to a beat, classify FOIs into first and second groups, align R-wave FOIs, mark R-wave FOIs, position P-wave detection windows, detect P-waves in the detection windows, align P-waves, identify P-wave outliers, etc., and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, CA signals, and processes the CA signals to detect arrhythmias. On a beat by beat basis, the ICM identifies first and second FOIs from a segment of the CA signal that corresponds to a current beat, classifies the current beat into first and second groups based on the relation between the first and second FOIs for the current beat, designates of the first or second groups to be a primary group based on the relation between the first and second groups, selects one of the first and second FOIs in the primary group as an R-wave FOI, positions a detection window over the CA signals based on the R-wave FOI, and detects P-waves in the P-wave detection window. The ICM also aligns R-wave FOIs, aligns the P-wave detection window, and identifies and rejects P-wave outliers.

Figure 2:
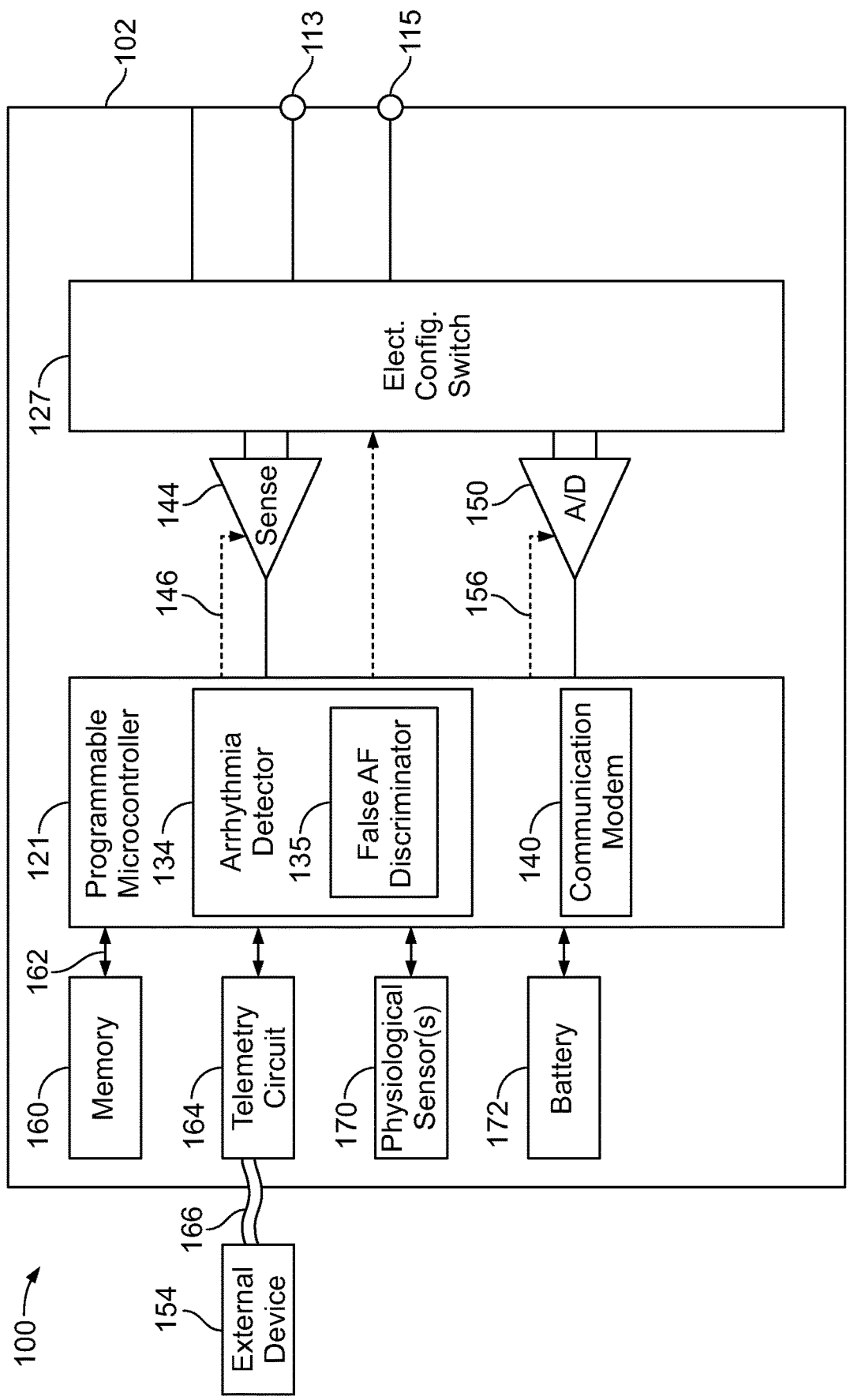
FIG. 2 shows a block diagram of the ICM formed in accordance with embodiments herein.

FIG. 2 shows a block diagram of the ICM 100 formed in accordance with embodiments herein. The ICM 100 may be implemented to monitor ventricular activity alone, or both ventricular and atrial activity through sensing circuitry. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with obtaining CA signals to identify AF episodes. Specifically, the microcontroller 121 can obtain a CA signal, and then identify first and second FOIs from a segment of the CA signal. The microcontroller from the segment of the CA signal can align an R-wave, align a P-wave, determine where to position a P-wave detection window, identify and reject outlier P-waves, designate primary groups and secondary groups to select R-wave FOIs, identify and differentiate peak values, including differentiating positive peak values from negative peak values, to designate the primary groups and secondary groups, or the like.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal 128 from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachycardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The arrhythmia detector may include a false AF discriminator 135 that may be implemented as hardware, software, or a combination of hardware and software. The false AF discriminator 135 analyzes obtained CA signals to modify the detection of the CA signals to account for potential errors that can result in the detection of false AFs. The false discriminator 135 aligns R-waves, aligns P-waves, determines the position and repositioning of a P-wave window, identifies R-wave FOIs, identifies P-wave outliers, etc. by analyzing segments of a CA signal. In particular, at least a portion of each of the methods and processes described in relation to FIGS. 4-7 are performed by the false AF discriminator 135. For example, the AF discriminator 135 can determine first or second groups based on positive and negative peak values of the CA signal. The first and second groups may then be designated as a primary group and a secondary group based on the population of each individual group as described in further detail herein. In another example, the false AF discriminator 135 can form a P-wave segment ensemble template based on P-waves detected, and compare a P-wave segment to the P-wave segment ensemble template to determine a signal to noise ratio of the P-wave segment. Based on the signal to noise ratio, the false AF discriminator 135 can reject the P-wave segment when the signal to noise ratio is above a threshold value.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuitry 144 selectively coupled to one or more electrodes that perform sensing operations, through the switch 127 to detect CA signals indicative of cardiac activity. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuitry 144 is connected to the microcontroller 121 and CA signals are digitized by the ND data acquisition system 150. The sensing circuitry 144 receives a control signal 146 from the microcontroller 121 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the A/D data acquisition system 150 directly coupled to the electrodes.

The ICM 100 further includes the analog-to-digital ND data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the CA signals that are analyzed for potential AF episodes using the methods and processes described herein.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch, and the like) that can be coupled over a network (e.g., the Internet) to a remote monitoring service, medical network, and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity signals, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

FIGS. 3A-3E illustrate example CA signal detection readings that can result in false AF episodes, and reduce accuracy of the AF detection. The processes and methodologies described in relation to FIGS. 4-7 reduce and/or prevent each of the false AF episode readings detailed in FIGS. 3A-3E.

Figure 3A:
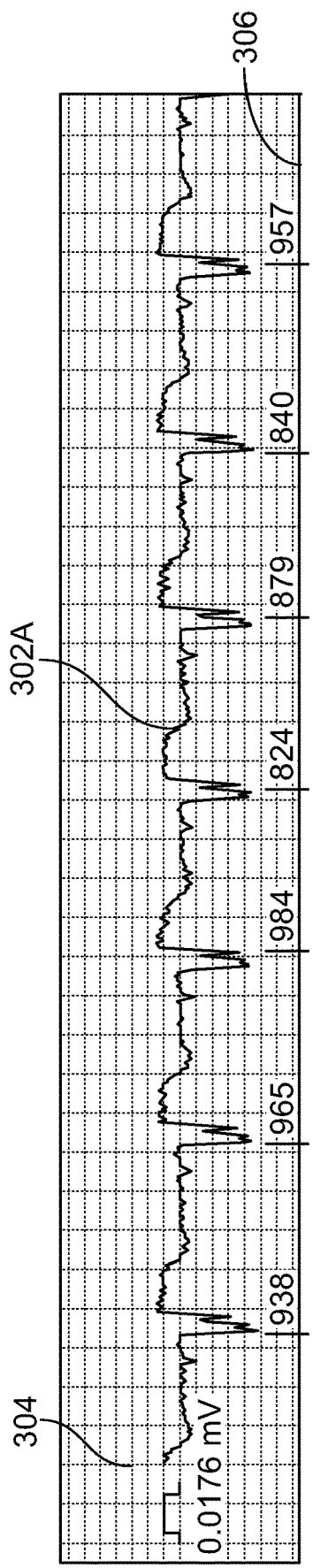
FIG. 3A shows a graph of cardiac activity signals over time in accordance with embodiments herein.

FIG. 3A illustrates an example first cardiac activity signal 302A when a bundle branch block (BBB) condition is presented. A BBB condition is a condition when a delay or blockage is provided in the pathway of electrical impulses that cause the heart to beat. The Y axis is provided in millivolts 304 while the X axis provides time 306. VS and the vertical tick represent the time point at which a R wave is being sensed. As illustrated, the BBB results in misaligned VS markers in the cardiac activity signal 302A.

Figure 3B:
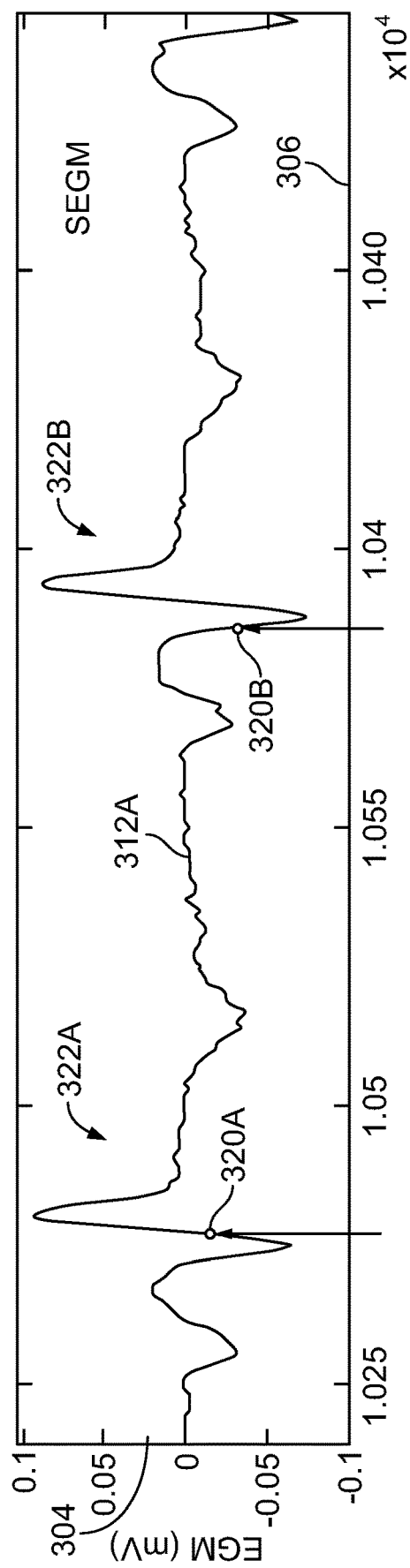
FIG. 3B shows a graph of cardiac activity signals over time in accordance with embodiments herein.

FIG. 3B illustrates a cardiac activity signal 312A with the graph illustrating voltage 304 over time 306 during biphasic QRS morphology, again resulting in misaligned markers: an R-wave marker 320A for a first heartbeat 322A, and a second R-wave marker 320B for a second heartbeat 322B.

As illustrated the R-wave markers 320A and 320B are misaligned during biphasic QRS morphology. Specifically, the first R-wave marker 320A for the first heartbeat 322A occurs during the positive deflection, whereas the second R-wave marker 320B for the second heartbeat 322B occurs during the negative deflection. The second R-wave marker 320B was placed earlier in the second heartbeat 322B because the initial negative deflection is steeper. In the first heartbeat 322A the negative deflection is not steep enough to reach the sensitivity level threshold for R wave sensing, consequently the first R wave marker 320A was placed later during the positive deflection phase.

Figure 3C:
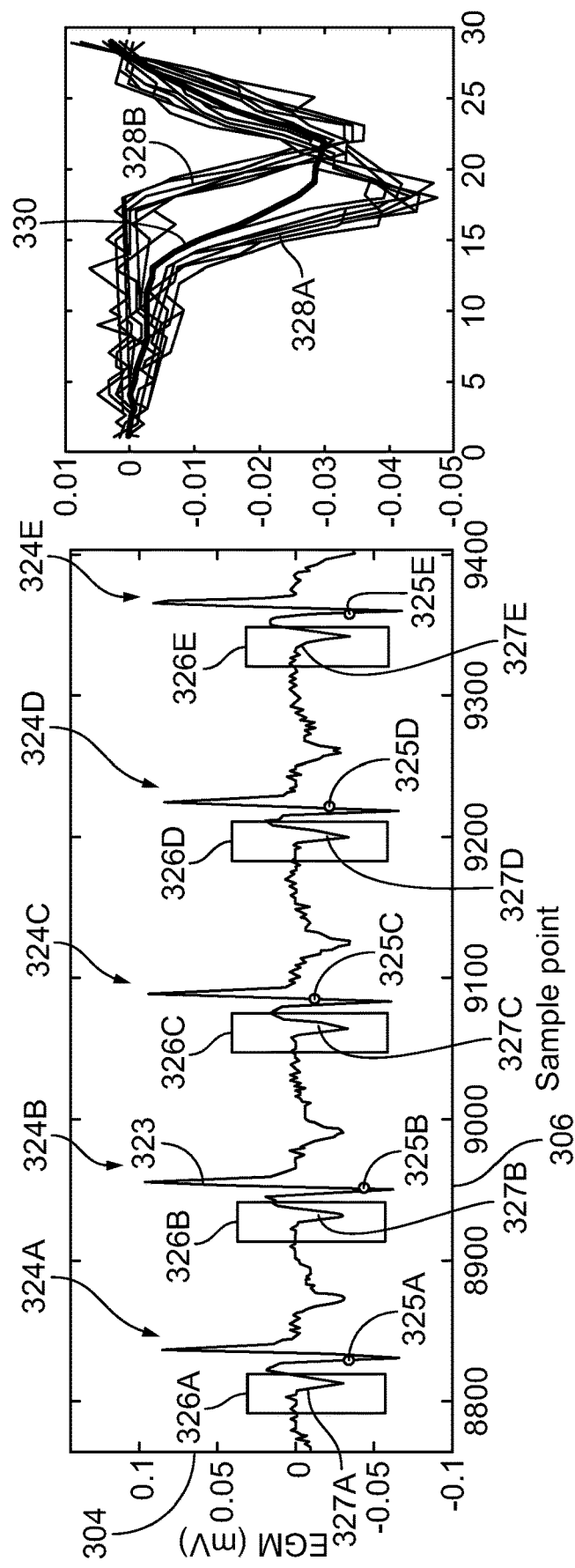
FIG. 3C shows a graph of cardiac activity signals over time in accordance with embodiments herein.

FIG. 3C shows how the misaligned R-wave markers (left graph) of FIG. 3B can negatively affect a P-wave analysis as provided in the P wave ensemble average template (right graph). The graph on the left again illustrates the cardiac signal 323 similar to that illustrated in the top graph of FIG. 3B with five complete heart beats illustrated instead of just the first two heartbeats. As such, the graph includes the Y axis 304 that is measured in mV and the X axis 306 represents time. Each beat 324A, 324B, 324C, 324D, and 324E (collectively 324A-E) in this graph is provided a R-wave marker 325A, 325B, 325C, 325D, and 325E (collectively 325A-E), where the R-wave markers 325A-E are misaligned. When using a P-wave analysis window 326A, 326B, 326C, 326D, and 326E (collectively 326A-E) based on the misaligned R-wave markers 325A-E results in incorrect P-wave analysis window placement. Specifically, some R-wave markers occur at the initial negative defection, with others occurring during the positive deflection. Because the P-wave analysis window uses the R-wave markers as the reference point, the P-wave segments 327A, 327B, 327C, 327D and 327E (collectively 327A-E) are misaligned into a first segment group 328A and a second segment group 328B in the ensemble average template (right graph). The ensemble average 330 resulting does not agree with the individual P-waves on either segment group 328A or 328B, causing inaccuracies in that can result in false AF detections.

Figure 3D:
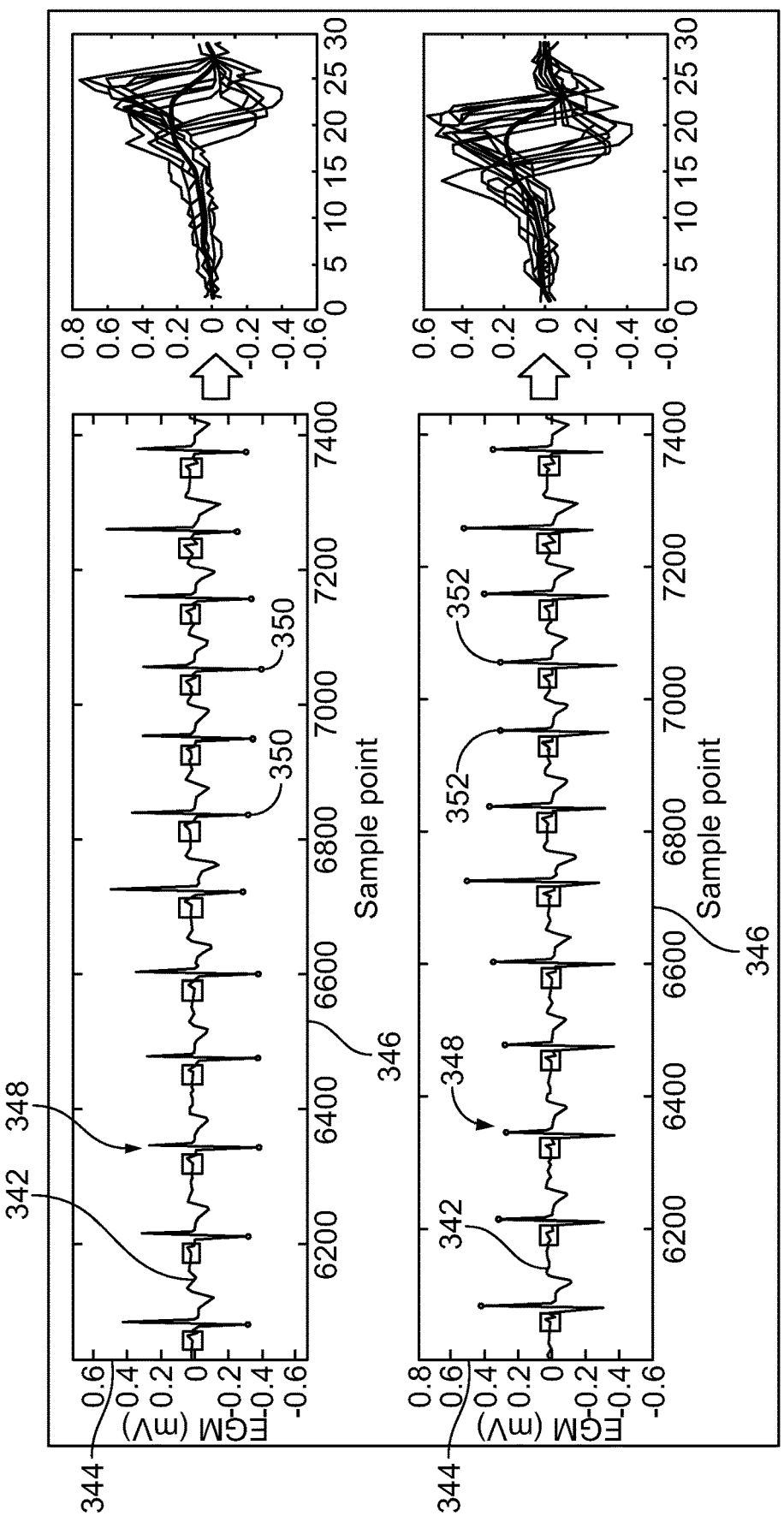
FIG. 3D shows a graph of cardiac activity signals over time in accordance with embodiments herein.

FIG. 3D illustrates another example where P-wave analysis may include inaccuracies. In this example, a cardiac signal 342 is illustrated on the top and bottom graphs where the Y axis 344 is measured in mV and the X axis 346 is measured in time. Again, plural R-wave markers are provided to heartbeats 348. Specifically, the top graph illustrates negative R-wave markers 350, while the bottom graph illustrates positive R-wave markers 352. Here, the positive R-wave markers 352 and negative R-wave markers are aligned. However, as illustrated in the ensemble average templates (right graphs), inaccuracies remain. Specifically, in this example, the P-R variations among individual P-wave segments results in the P-wave analysis window that is placed based on the R-wave markers, and not placed in the correct location for P-wave analysis. The inconsistent ensemble average templates illustrate these inconsistencies.

Figure 3E:
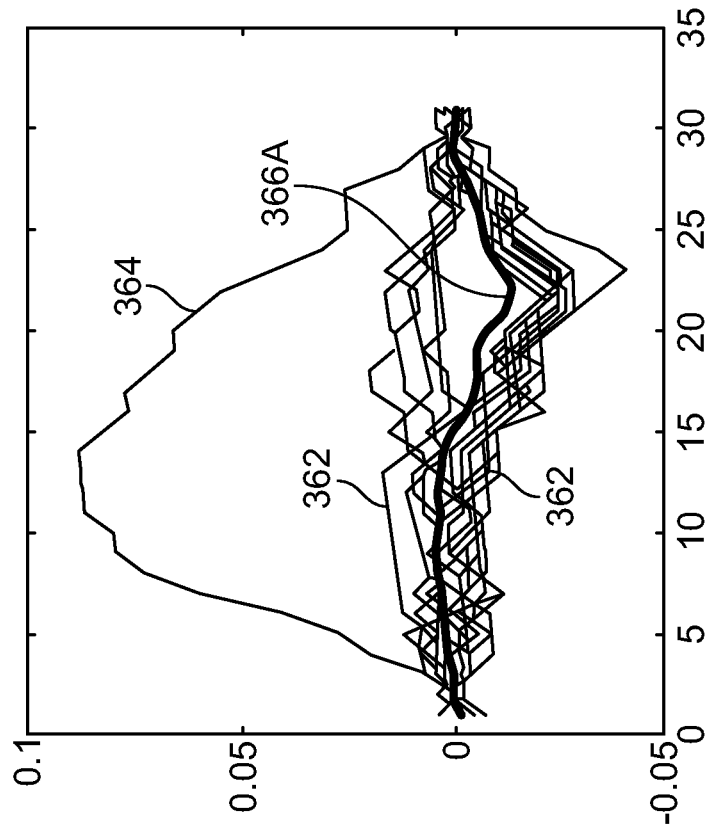
FIG. 3E shows a graph of an ensemble of cardiac activity signals over time in accordance with embodiments herein.
Figure 3E:
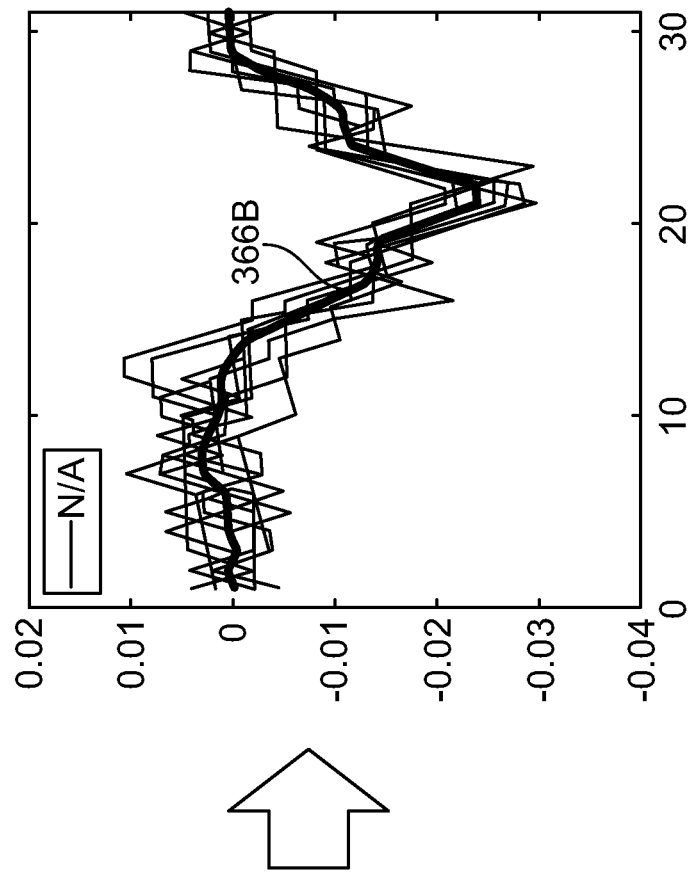

FIG. 3E meanwhile illustrates the affect an outlier P-wave segment can have on an ensemble average template. Each graph illustrated shows P-wave segments 362 that have been generated from using R-wave markers for P-wave analysis. The graph on the left provides an outlier P-wave segment 364 that is removed from the graph on the right. Based simply on this one outlier P-wave segment, the ensemble averaged P-wave template 366A of the right graph is significantly different than the ensemble averaged P-wave template 366B of the left graph that has removed the outlier P-wave segment 364. In this example, the P-wave amplitude difference is 27 µV, providing a detectable difference as a result of the outlier P-wave segment 364.

Figure 4:
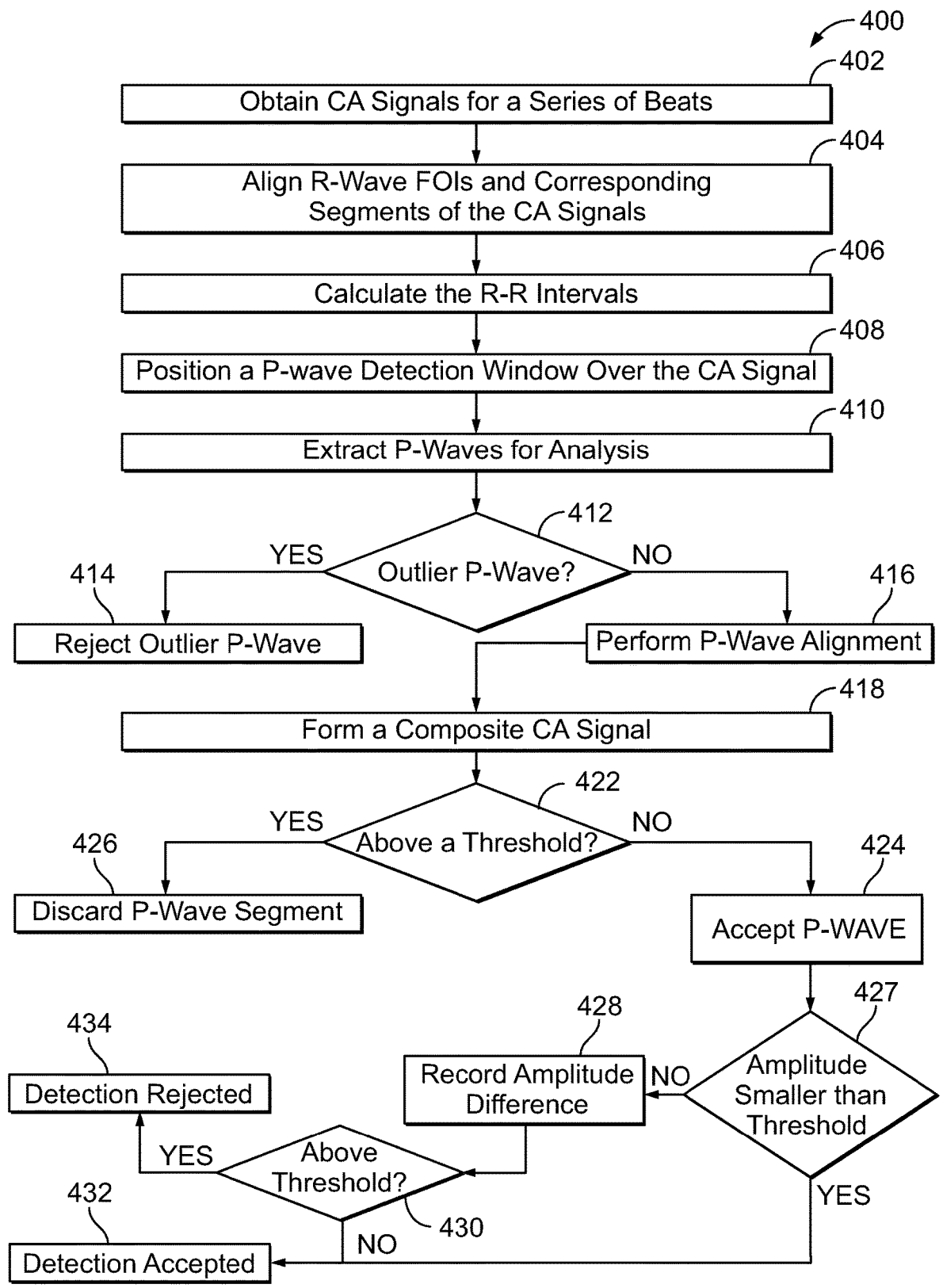
FIG. 4 illustrates a block diagram of a P-wave detection process implemented in accordance with embodiments herein.

FIG. 4 illustrates a block diagram of a P-wave detection process implemented in accordance with embodiments herein. At 402, one or more processors obtain CA signals for a series of beats. In one example, the CA signals are far field CA signals. Each individual CA signal has features of interest (FOIs) that may include R-wave segments, P-wave segments, or other segments or portions of the individual CA signal.

In one embodiment, when the P-wave detection process is implemented in real time on a beat by beat basis by an ICM, the processors may receive the CA signals in real time from an onboard R-wave detection process. Additionally or alternatively, while still implemented on the ICM, the P-wave detection process may obtain the CA signals from a section of memory in the ICM, and analyze the CA signals for P-waves, such as in connection with an arrhythmia first pass detection process or second pass confirmation process. Additionally or alternatively, the P-wave detection process may be implemented on a local external device (e.g., patient smart phone, tablet device, laptop computer) while or after CA signals are downloaded from an ICM. When implemented on a local external device, the P-wave detection process may analyze the CA signals for P-waves in connection with an arrhythmia confirmation process. Additionally or alternatively, the P-wave detection process may be implemented at a remote server while the remote server is performing an arrhythmia confirmation process upon CA signals received from an ICM and/or local external device.

At 404, the one or more processors align R-wave FOIs and the corresponding segments of the CA signals with one another for at least a portion of the series of beats based on the R-wave FOIs.

Figure 5:
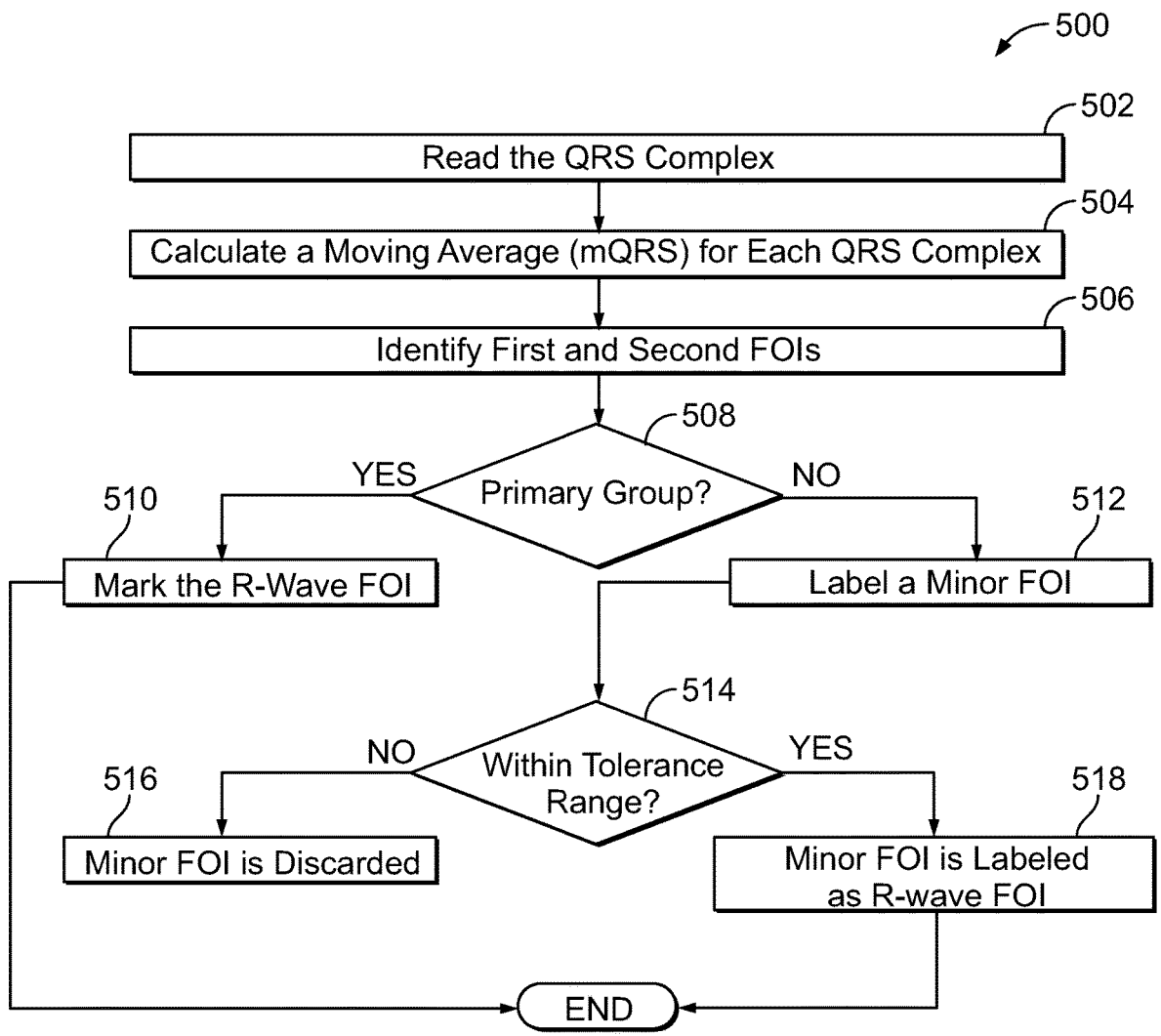
FIG. 5 illustrates a block diagram of a R-wave alignment process in accordance with embodiments herein.

In order to provide R-wave FOI alignment, attention is directed to FIG. 5 as one example of a method 500 of aligning R-wave FOIs. At 502, the QRS complex (corresponding segment) from each R-wave marker in an analysis window is read. At 504, the one or more processors calculate a moving average (mQRS) for each QRS complex. In one example, the moving average is a five (5) point moving average.

At 506, the one or more processors identify first and second FOIs from a segment of a CA signal that corresponds to a current beat. In one example, positive and negative peak values of the QRS complex are identified as the respective first and second FOIs and recorded, along with the position of the peak values in the moving average. At 508, the current beat is classified into one of first and second groups based on a relation between the first and second FOIs. In one example, the first group is populated with QRS complexes where the positive peak value is larger than the negative peak value, while the second group is populated with QRS complexes that have a negative peak value that is larger than a positive peak value.

At 508, one of the first group or the second group is designated as a primary group based on the relation between the first and second groups. Specifically, in one example the relation represents a popularity relation, and the one of the first group and second group that has the largest population of beats is designated as the primary group. For example, a popularity relation represents a relation between a count of a number of FOIs in the first group and the count of the number of FOIs in the second group.

So, when the first group and second group are based on positive and negative peak value as described above, the group that is most populated becomes the primary group. Meanwhile, the least populated group becomes the secondary group.

In an example, when five beats are classified, and four of the beats have a positive peak value that is larger than the negative peak value that are classified in the first group, and only one beat has a positive peak value that is smaller than the negative peak value that is classified in the second group, the first group being the most populated group would be designated as the primary group. Meanwhile the second group being the least populated would be designated as the secondary group. Alternatively, if in the five beats classified, only one of the beats has a positive peak value that is larger than the negative peak value that is classified in the first group, and four beats have a positive peak value that is smaller than the negative peak value that are classified in the second group, the second group being the most populated group would be designated as the primary group, and the first group being the least populated would be the secondary group.

In yet another example, if six beats are classified and the same number of beats are classified in each group, the one or more processor designates either the first group or second group as the primary group. For instance, the one or more processors may default that when an equal number of beats are within each group, a group where the positive peak value is larger than the negative peak value is selected as the primary group. Alternatively, the group where the positive peak value is smaller than the negative peak value may be selected as the primary group.

At 510, for the beats in the primary group, the one or more processors mark a select one of the first and second FOIs as the R-wave FOI. In an example when the primary group has a positive peak value that is greater than the negative peak value, and the first FOI is a positive peak value, the first FOI is selected. Alternatively, when the primary group has a positive peak value that is less than the negative peak value, and the second FOI is a negative peak value, the second FOI is selected.

At 512, for the beats in the secondary group, the first and second FOIs are compared, and one of the first or second FOIs is labeled as a minor FOI for the corresponding beat. In an example, when a positive peak value (first FOI) is greater than a negative peak value (second FOI) within a secondary group, the negative peak value is labeled as a minor FOI. Alternatively, if the positive peak value is less than the negative peak value in the secondary group, the positive peak value is labeled as the minor FOI.

At 514, a determination is made if the first FOI is within a tolerance range of the second FOI. In one example, when the secondary group has a positive peak value (first FOI) greater than a negative peak value (second FOI), and the negative peak value is labeled as the minor FOI, a difference between the positive and negative peak values is determined. That difference between peak values is then compared to a tolerance range. In one example, the tolerance range is the smaller peak value (here the negative peak value) greater than 80% of the larger peak value (here the positive value). In other examples, the tolerance range may be when the smaller peak value is greater than 70%, 90%, 50%, etc. than the larger peak value. In each instance, the percentage is utilized to determine if the first FOI is within a tolerance range of the second FOI.

If at 514, a determination is made that the first FOI is not within the tolerance range of the second FOI, at 516, the minor FOI is rejected and not used. If at 514, a determination is made that the first FOI is within the tolerance range of the second FOI, at 518, the minor FOI is labeled as an R-wave FOI.

Figure 6A:
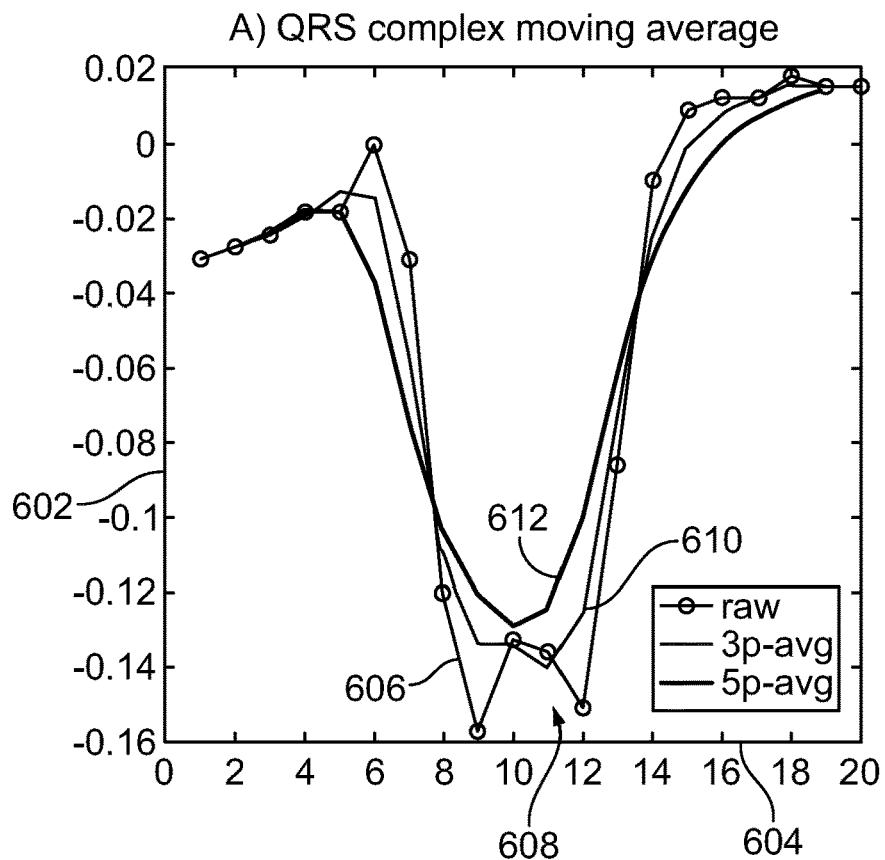
FIG. 6A illustrates a graph of a QRS complex moving average over time in accordance with embodiments herein.
Figure 6B:
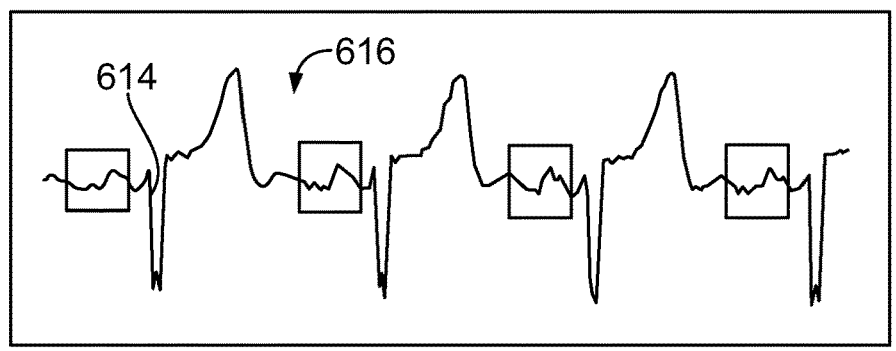
FIG. 6B illustrates a graph of cardiac activity signals over time in accordance with embodiments herein.
Figure 6C:
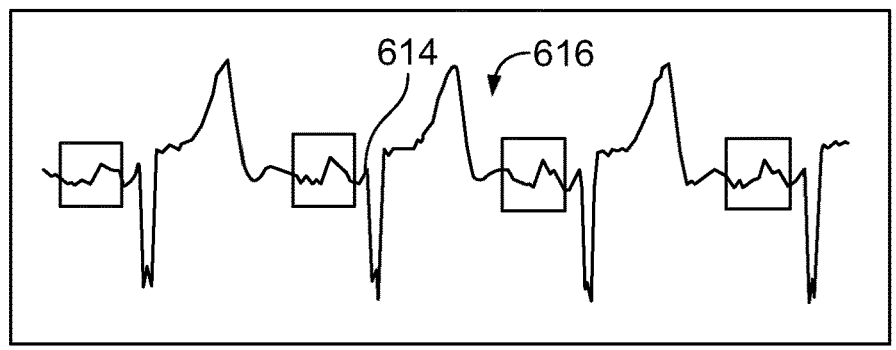
FIG. 6C illustrates a graph of cardiac activity signals over time in accordance with embodiments herein.

As a result of the method of FIG. 5, the R-wave of a beat is aligned. FIGS. 6A-6C illustrate the how the method of FIG. 5 may be used to properly align an R-wave using the method of FIG. 5 to remove a notch in the CA signals, representing a non-noise artifact displacement (NAD), due to bundle branch block. FIG. 6A illustrates a portion of a heartbeat measured in millivolts 602 over time 604. The graph of FIG. 6A includes a raw QRS complex 606 that has a double-hump, or the notch 608 that typically could cause a NAD. Additionally provided in the graph of FIG. 6A is first modified QRS complex 610 that utilizes the method described in relation to FIG. 5 utilizing a three (3) sample point moving combination or average, and a second modified QRS complex 612 that utilizes the method described in relation to FIG. 5 utilizing a five (5) sample point moving combination or average.

The corresponding graph of FIG. 6B illustrates the R-wave peaks 614 of heartbeats 616 determined when not using the method of FIG. 5. As the graph illustrates, some of the R-wave peaks are located at the first hump, while other R-wave peaks are placed at the second hump, presenting misalignment. Meanwhile, FIG. 6C illustrates the R-wave peaks 614 of the same heartbeats 616 determined when using the method of FIG. 5 utilizing a 5-point moving average. As illustrated, the R-wave peaks 614 are consistent in position across each individual beat. In this manner, the moving combination is configured to at least partially remove the NAD due to a physiologic condition. In one example, the physiologic condition is a bundle branch block.

With attention back to the method of FIG. 4, after R-wave alignment at 404, at 406, the one or more processors calculate the R-R intervals. Specifically, after the R-wave alignment, the difference between the identified R-wave peak and the original device R-wave marker position is calculated in a beat-by-beat manner. The median difference is used to adjust the boundary of the P-wave segment window. For example, when the default P-wave segment window is from 350 msec to 50 msec prior to the R-wave marker, the P-Wave segment is moved to between 350 msec plus the median difference to 50 msec plus the median difference. The adjustment avoids including part of the QRS complex in the P-wave segment. In particular, because the R-waves are aligned before the R-R intervals are determined, more consistent R-R interval calculations are provided.

At 408, the one or more processors positions a P-wave detection window over the CA signal in connection with at least a portion of the beats based on the R-wave FOI for the corresponding beat. To position the P-wave search window, in one example, the processors use a determined R-wave marker in a corresponding beat as a reference point, and adjustment of the P-wave segment is provided as described above.

At 410, P-waves in the P-wave detection window over the CA are detected for analysis. Specifically, based on the R-R alignment, the beats are selected for P-wave analysis. Once the selection is made, a P-wave segment is extracted by using a P-wave detection window to locate the P-wave segment.

At 412, the one or more processors identify beats that have outlier P-waves from the extracted P-waves. Specifically, P-waves having peak to peak amplitudes that are not within a pattern of a distribution of P-wave peak to peak amplitudes for at least a portion of the beats are considered outliers. In one example, a peak-to-peak amplitude is calculated in each individual P-wave, and P-waves with peak-to-peak amplitudes greater than a threshold are excluded from the remaining determinations. In one example, the threshold is 0.1 mV. In addition, an average peak-to-peak amplitude (P2Pavg) is calculated, and P-waves with peak-to-peak amplitudes that are either >2×P2Pavg or <0.5× P2Pavg are also excluded from additional determinations.

If at 412, a P-wave is identified as an outlier P-wave, at 414, the outlier P-wave is rejected and not used for analysis, preventing a potential false arrythmia detection. By providing an outlier P-wave check after the R-R intervals are calculated, the analysis is further refined, reducing false AF detections. If at 412, a P-wave is not identified as an outlier P-wave, then at 416, P-wave alignment is performed.

Figure 7:
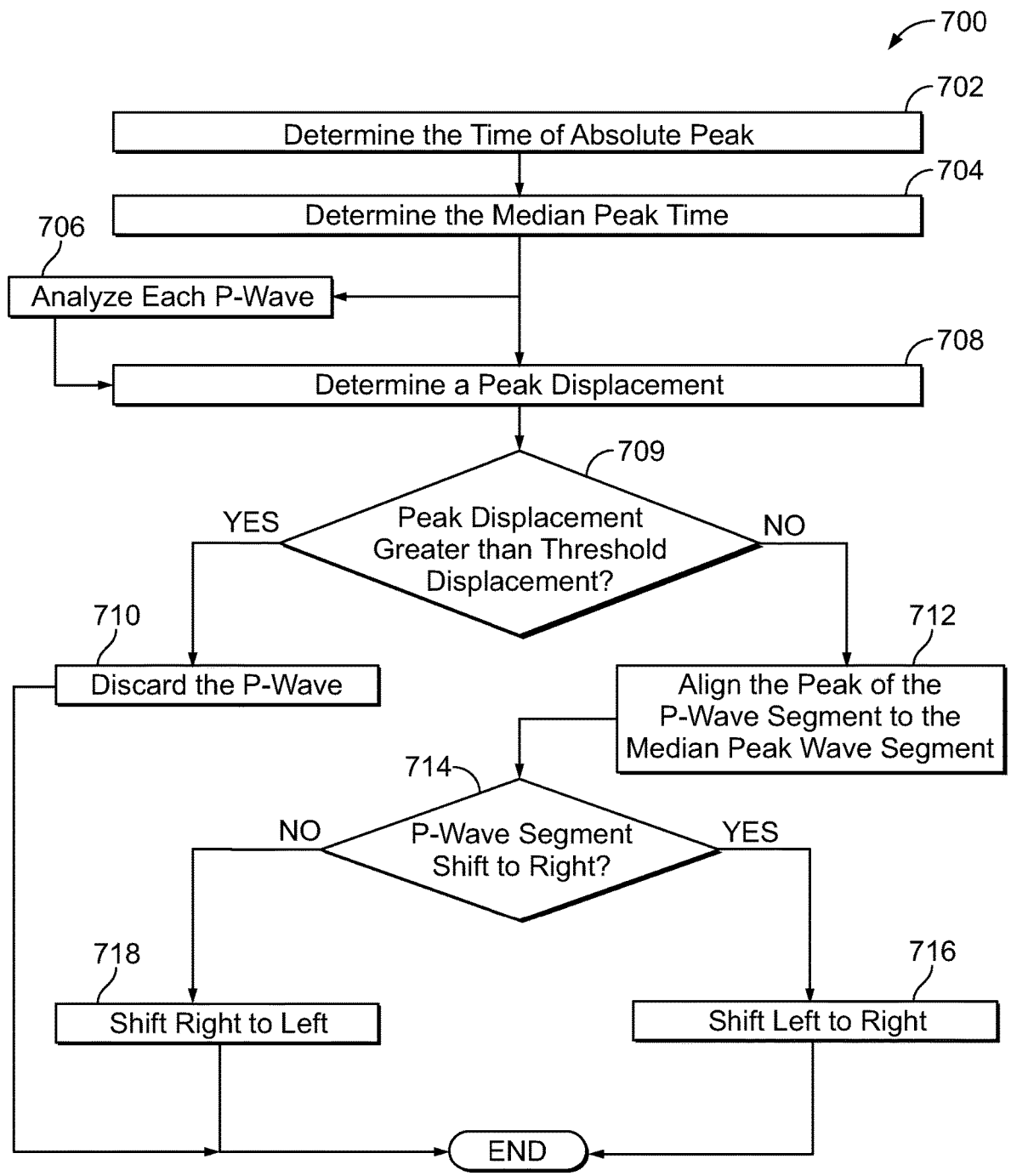
FIG. 7 illustrates a block diagram of a P-wave alignment process in accordance with embodiments herein.

In one example, FIG. 7 illustrates a method 700 of performing P-wave alignment. By performing P-wave alignment, additional accuracy is achieved. For example, when P-R interval variations for a patient such as illustrated in FIG. 3D is present, even when R-waves are aligned, reading inaccuracies may occur.

At 702, the one or more processors determine the time of absolute peak for a given P-wave. In this manner, the P-R interval is determined. At 704, the one or more processors determine the median peak time in all P-waves. Specifically, numerous beats are analyzed to determine median peak time of all the P-waves. In one example, more than three (3) P-waves are analyzed. In another example, more than five (5) P-waves are analyzed. The reason that a median peak time is utilized instead of an average is to guard against and eliminate the effect of P-wave outliers. For example, when four peak times are nearly identical, and one peak time varies, instead of the average being used causing the one varied peak time to skew the average, by using the median peak time, a more accurate result occurs.

At 706, optionally, one or more processors may analyze each P-wave a second time. In particular, in some instances, P-waves may be removed during initial analysis. At 708, one or more processors determine a peak displacement between the peak time of each P-wave and the determined median peak time.

At 709, one or more processors determine if the peak displacement is greater than a threshold displacement. In one example, the threshold displacement is 35 ms. Alternatively, the threshold displacement may be in a range between 25 ms and 45 ms. At 709, if the threshold displacement is exceeded, at 710, the one or more processors reject the P-wave from use in additional analysis. By rejecting, the P-wave is unable to cause inaccuracies that can result in a false AF detection. At 709, if the threshold displacement is not exceeded, at 712 the one or more processors shift the P-wave segment to align the peak of the P-wave segment to the median peak wave segment. The P-wave segment may be shifted to the left or to the right. Still, by aligning the peak of the P-wave segment with the median peak of all the P-waves, alignment for measurements is improved.

At 714, the one or more processors determine if the P-wave segment shifts from left to right, or right to left. If the P-wave segment shifts from left to right at 714, at 716, the one or more processors set an initial left boundary voltage value for new samples added on the left side. Similarly, if at 714 the P-wave segment shifts from right to left, at 718 the one or more processors set an initial right boundary voltage value for the new samples added on the right side. In each instance, the P-wave is shifted to account for differences in the P-R interval that cannot otherwise be addressed.

With attention back to the method of FIG. 4, at 418, the one or more processors calculate a moving combination for the CA signals to form a composite CA signal. In one example, the composite CA signal is considered a P-wave segment ensemble.

At 422, each P-wave is compared to the ensemble average template by comparing their amplitude difference. If the amplitude difference is less than a threshold, at 424 the P-wave is accepted; otherwise, at 426, the P-wave is rejected or discarded from the remaining steps. Thus, using only the remaining P-waves accepted, the amplitude of a P-wave segment ensemble is calculated at 427. Specifically, the composite CA signal is redetermined using the remaining P-waves, and the peak-to-peak amplitude of the final composite CA signal is used as the final amplitude of P-wave segment ensemble. If the final amplitude of P-wave ensemble is smaller than a threshold, the initial detection is accepted. If the final amplitude of P-wave ensemble is greater than the threshold, proceed to 428.

At 428 the amplitude difference is recorded as a noise amplitude level for this P-wave. Once all P-waves go through step 422, using only the remaining P-waves, at 430 a signal-to-noise ratio is calculated. Specifically, the average value of noise amplitude level among the remaining P-waves are calculated as the final signal-to-noise ratio. The final signal-to-noise ratio is checked to determine if the final signal-to-noise ratio is also smaller than a fixed threshold. In one example, the fixed threshold may be 5. If at 430 the final signal-to-noise ratio is smaller than the fixed threshold, at 432 the initial detection is accepted. If at 430 the final signal-to-noise ratio is equal to or greater than the fixed threshold, at 434 the initial arrhythmia detection is rejected or discarded.

Once the P-wave segment ensemble is formed, the R-wave FOIs and/or P-waves may be utilized to detect an arrhythmias. One example of how a P-wave segment ensemble may be used to reject an AF detection is detailed in U.S. Ser. No. 15/973,107 filed May 7, 2018, entitled Method and System to Detect P-Waves in Cardiac Arrhythmic Patterns that is incorporated by reference in full herein.

The operations of FIG. 4 may be applied on-board an ICM in real-time or near-real-time, and may be used as an integrated part of an AF determination/detection process, rather than a verification process to be applied after AF detection. When applied in an onboard real time implantation, the beat selection process of FIG. 4 would be initiated as described above once an AF detection process reaches some intermediate threshold, such that P-wave ensemble averaging may not be required for every beat, but still begins before an AF trigger. By way of example, a maximum number of beats may be defined for the P-wave segment ensemble, such as when utilizing a memory buffer of 32 beats. The beats recorded by the memory buffer need not be consecutive but rather may include only beats that fit the beat selection criteria and are less than some threshold number of beats (or time duration) in the past. Additionally or alternatively, the buffer may only store beats that occurred a predetermined number of cardiac cycles prior to a current beat (e.g., no more than 64 beats prior to the current beat). The buffer may also reject any beats beyond a predetermined total (e.g., 32 beats). For example, the processors may maintain a running sum beat by beat as new P-wave segments are added to and subtracted from the buffer, rather than computing a full average every time. The remaining processing steps for P-wave detection as described above are carried out unchanged.

Additional steps may be performed to reduce computation burden of these enhancements. For example, a pre-evaluation may be conducted before running the enhancements. The a few beats can be selected to check the signal amplitudes in their P-wave segment. Only if the signal amplitudes are in the physiological range of true P-waves do the methodologies and processes proceed.

Figure 8:
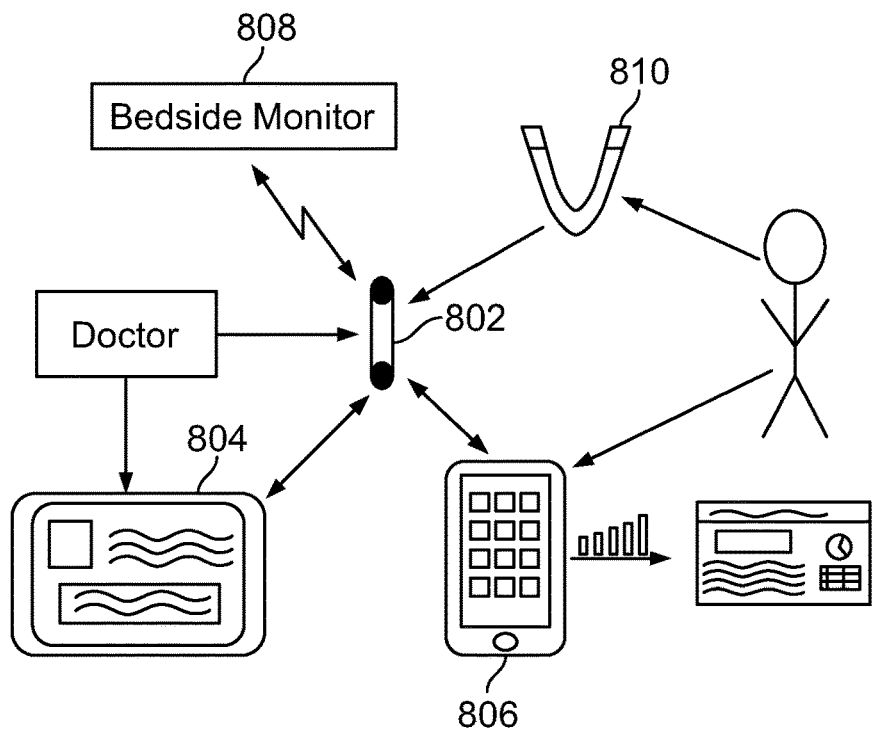
FIG. 8 illustrates a system level diagram indicating potential devices and networks in which the methods and systems herein may be utilized in accordance with embodiments herein.

FIG. 8 illustrates a system level diagram indicating potential devices and networks that utilize the methods and systems herein. For example, an implantable cardiac monitoring device (ICM) 802 may be utilized to collect a cardiac activity signals, and AF detection to various local external devices, such as a tablet device 804, a smart phone 806, a bedside monitoring device 808, a smart watch and the like. The devices 804-808 include a display to present the various types of CA signals, markers, statistics, diagnostics, and other information described herein. The ICM 802 may convey the CA signal and AF detection over various types of wireless communications links to the devices 804, 806 and 808. The ICM 802 may utilize various communications protocols and be activated in various manners, such as through a Bluetooth, Bluetooth low energy, WiFi or other wireless protocol. Additionally or alternatively, when a magnetic device 810 is held next to the patient, the magnetic field from the device 810 may activate the ICM 802 to transmit the cardiac activity signals and AF detection determinations to one or more of the devices 804-808.

The processes described herein for analyzing the CA signal and/or provide AF detection may be implemented on one or more of the devices 804-808. Additionally or alternatively, the ICM 802 may also implement confirmatory processes. The devices 804-808 may present the CA signal and AF detection determination to clinicians in various manners. As one example, AF markers may be illustrated on EGM signal traces. AF and sinus markers may be presented in a marker channel that is temporally aligned with original or modified CA signals. Additionally or alternatively, the duration and heart rate under AF may be formatted into histograms or other types of charts to be presented alone or in combination with CA signals.

Figure 9:
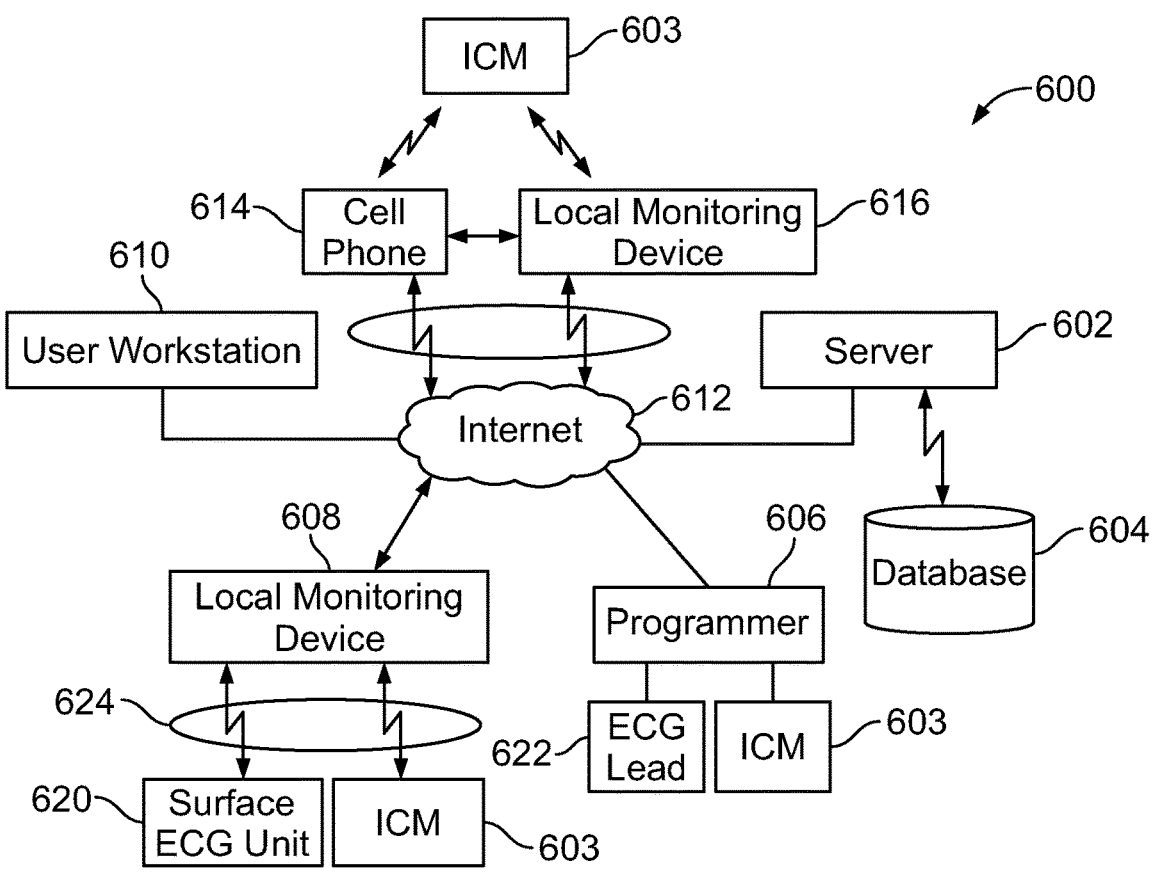
FIG. 9 illustrates a distributed processing system in accordance with embodiments herein.

FIG. 9 illustrates a distributed processing system 900 in accordance with embodiments herein. The distributed processing system 900 includes a server 902 connected to a database 904, a programmer 906, a local monitoring device 908 and a user workstation 910 electrically connected to a network 912. Any of the processor-based components in FIG. 9 (e.g., workstation 910, cell phone 914, local monitoring device 916, server 902, programmer 906) may perform the processes discussed herein.

The network 912 may provide cloud-based services over the internet, a voice over IP (VoIP) gateway, a local plain old telephone service (POTS), a public switched telephone network (PSTN), a cellular phone based network, and the like. Alternatively, the communication system 912 may be a local area network (LAN), a medical campus area network (CAN), a metropolitan area network (MAN), or a wide area network (WAM). The communication system 912 serves to provide a network that facilitates the transfer/receipt of data and other information between local and remote devices (relative to a patient). The server 902 is a computer system that provides services to the other computing devices on the network 912. The server 902 controls the communication of information such as CA signal waveforms, bradycardia episode information, asystole episode information, AF episode information, markers, heart rates, and device settings. The server 902 interfaces with the network 912 to transfer information between the programmer 906, local monitoring devices 908, 916, user workstation 910, cell phone 914 and database 904. The database 904 stores information such as CA signals and CA signal waveforms, AF episode information, AF statistics, diagnostics, markers, heart rates, device settings, and the like, for a patient population. The information is downloaded into the database 904 via the server 902 or, alternatively, the information is uploaded to the server 902 from the database 904. The programmer 906 may reside in a patient's home, a hospital, or a physician's office. The programmer 906 may wirelessly communicate with the ICM 903 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 906 to the ICM 903. The programmer 906 is able to acquire ECG from surface electrodes on a person (e.g., ECGs) 922, electrograms (e.g., EGM) signals from the ICM 903, and/or CA signals and CA signal waveforms, AF episode information, AF statistics, diagnostics, markers, atrial heart rates, device settings from the ICM 903. The programmer 906 interfaces with the network 912, either via the internet, to upload the information acquired from the surface ECG unit 920, or the ICM 903 to the server 902.

The local monitoring device 908 interfaces with the communication system 912 to upload to the server 902 one or more of CA signals and CA signal waveforms, AF episode information, AF statistics, diagnostics, markers, heart rates, sensitivity profile parameter settings and detection thresholds. In one embodiment, the surface ECG unit 920 and the ICM 903 have a bi-directional connection 924 with the local RF monitoring device 908 via a wireless connection. The local monitoring device 908 is able to acquire cardiac signals from the surface of a person, CA signals and CA signal waveforms and other information from the ICM 903, and/or heart rates, and device settings from the ICM 903. On the other hand, the local monitoring device 908 may download the data and information discussed herein from the database 904 to the surface ECG unit 920 or the ICM 903.

The user workstation 910 may be utilized by a physician or medical personnel to interface with the network 912 to download cardiac activity data and other information discussed herein from the database 904, from the local monitoring devices 908, 916, from the ICM 903 or otherwise. Once downloaded, the user workstation 910 may process the CA signals in accordance with one or more of the operations described above. The user workstation 910 may upload/push settings (e.g., sensitivity profile parameter settings), ICM instructions, other information, and notifications to the cell phone 914, local monitoring devices 908, 916, programmer 906, server 902 and/or ICM 903. For example, the user workstation 910 may provide instructions to the ICM 903 in order to update sensitivity profile parameter settings when the ICM 903 declares too many false AF detections.

The processes described herein in connection with analyzing CA signals for more accurate AF detection may be performed by one or more of the devices illustrated in FIG. 9, including but not limited to the ICM 903, programmer 906, local monitoring devices 908, 916, user workstation 910, cell phone 914, and server 902. The process described herein may be distributed between the devices of FIG. 9.

In connection with embodiments herein, the cloud-based approach allows an AF episode that is detected by the ICM using the detection algorithms, to be passed through the local external device and stored at the server 902, database 904, workstation 910 or at another remote device within the cloud-based system. When an individual ICM is interrogated for a CA signal, the interrogation device would also request, from the cloud-based system, any additional information, such as any confirmation logs stored elsewhere within the system. For example, when an external device, such as a cell phone 914, local monitoring device 908, 916 and/or programmer 906 interrogate an individual ICM, the cell phone 914, local monitoring device 908, 916 and/or programmer 906 would also broadcast an ICM data supplement request over the cloud-based system. The ICM data supplement request requests additional data/information related to the individual ICM (e.g., based on the ICM serial number). In response thereto, the server 902 and/or other remote system may provide, to the requesting device, one or more confirmation logs or other information regarding past operation of the ICM.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A computer implemented method for detecting arrhythmias in cardiac activity, comprising:
    under control of one or more processors configured with specific executable instructions,
    obtaining far field cardiac activity (CA) signals for one or more beats;
    applying a detection process, to the CA signals, to obtain a device marker;
    identifying a first feature of interest (FOI) within an analysis window of a segment of the CA signal;
    calculating a difference between the first FOI and the device marker;
    adjusting a feature detection window with respect to the CA signals based on the difference;
    detecting a second FOI in the feature detection window over the CA signals; and
    rejecting an arrhythmia detection based on the second FOI detected.

2. The method of claim 1, wherein the detection process is an R-wave detection process, the device marker is a device R-wave marker, and the first FOI is an R-wave FOI.

3. The method of claim 2, wherein the feature detection window is a P-wave detection window, the second FOI is a P-wave and the method rejects the arrhythmia detection based on the P-wave detected.

4. The method of claim 3, wherein the analysis window positioned, relative to the CA signals, based on the R-wave marker.

5. The method of claim 3, wherein the P-wave detection window is originally positioned, with respect to the CA signals, based on a location of the device R-wave marker, the adjusting operation including adjusting one or more boundaries of the P-wave detection window, with respect to the CA signals, based on the difference.

6. The method of claim 3, wherein the difference is calculated in a beat-by-beat manner.

7. The method of claim 6, further comprising determining a median peak time for the P-waves detected; and determining a peak displacement between a peak time of each of the P-waves detected and the determined median peak time.

8. The method of claim 3, further comprising calculating a moving combination for the CA signals to form a composite CA signal, the moving combination configured to at least partially remove non-noise artifact displacement (NAD) due to a physiologic condition, the identifying, classifying, adjusting and detecting based on the composite CA signals.

9. The method of claim 8, wherein the moving combination is configured to at least partially remove a notch in the CA signals, representing the NAD.

10. The method of claim 3, further comprising identifying the beats that have outlier P-waves, the outlier P-waves having peak to peak amplitudes that are not within a pattern of a distribution of P-wave peak to peak amplitudes for at least a portion of the beats.

11. The method of claim 3, further comprising repeating the obtaining, identifying, calculating, adjusting, and detecting for multiple beats to detect multiple P-waves, and shifting a peak of a first P-wave of the multiple P-waves to align with a median peak of the multiple P-waves detected.

12. A system for detecting arrhythmias in cardiac activity, comprising:
memory to store specific executable instructions;
one or more processors configured to execute the specific executable instructions to:
obtain far field cardiac activity (CA) signals for one or more beats;
apply a detection process, to the CA signals, to obtain a device marker;
identify a first feature of interest (FOI) within an analysis window of a segment of the CA signal;
calculate a difference between the first FOI and the device marker;
adjust a feature detection window with respect to the CA signals based on the difference;
detect a second FOI in the feature detection window over the CA signals; and
reject an arrhythmia detection based on the second FOI detected.

13. The system of claim 12, wherein the detection process is an R-wave detection process, the device marker is a device R-wave marker, and the first FOI is an R-wave FOI.

14. The system of claim 13, wherein the feature detection window is a P-wave detection window, the second FOI is a P-wave and the one or more processors is further configured to reject the arrhythmia detection based on the P-wave detected.

15. The system of claim 14, wherein the one or more processors are further configured to originally position the P-wave detection window, with respect to the CA signals, based on a location of the device R-wave marker, and to adjust one or more boundaries of the P-wave detection window, with respect to the CA signals, based on the difference.

16. The system of claim 14, wherein the one or more processors are further configured to calculate the difference in a beat-by-beat manner for multiple beats.

17. The system of claim 16, wherein the one or more processors are further configured to determine a median peak time for the P-waves detected; and determine a peak displacement between a peak time of each of the P-waves detected and the determined median peak time.

18. The system of claim 17, wherein the one or more processors are further configured to determine when the peak displacement between the peak time of each of the P-waves detected exceeds a threshold displacement.

19. The system of claim 16, wherein the one or more processors are further configured to identifying the beats that have outlier P-waves, the outlier P-waves having peak to peak amplitudes that are not within a pattern of a distribution of P-wave peak to peak amplitudes for at least a portion of the beats.

20. The system of claim 12, wherein the one or more processors are further configured to execute the specific executable instructions to position the analysis window, relative to the CA signals, based on the device marker.

* * * * *